(12) United States Patent
Zhou et al.

(10) Patent No.: US 7,951,745 B2
(45) Date of Patent: *May 31, 2011

(54) CATALYST FOR HYDROCRACKING HYDROCARBONS CONTAINING POLYNUCLEAR AROMATIC COMPOUNDS

(75) Inventors: Bing Zhou, Cranbury, NJ (US); Zhenhua Zhou, Pennington, NJ (US); Zhihua Wu, Lawrenceville, NJ (US)

(73) Assignee: Wilmington Trust FSB, Minneapolis, MN (US)

( * ) Notice: Subject to any disclaimer, the term of this patent is extended or adjusted under 35 U.S.C. 154(b) by 637 days.

This patent is subject to a terminal disclaimer.

(21) Appl. No.: 11/968,861

(22) Filed: Jan. 3, 2008

(65) Prior Publication Data

US 2009/0173665 A1    Jul. 9, 2009

(51) Int. Cl.
*C07F 11/00* (2006.01)
*C07F 15/00* (2006.01)
*C10G 47/02* (2006.01)

(52) U.S. Cl. ......... 502/171; 502/150; 208/108; 208/112

(58) Field of Classification Search ................. 208/108, 208/112; 502/150, 171; 556/42, 44, 45, 556/49, 51, 54, 57, 61, 138, 146
See application file for complete search history.

(56) References Cited

U.S. PATENT DOCUMENTS

| | | |
|---|---|---|
| 3,362,972 A | 1/1968 | Kollar |
| 3,578,690 A | 5/1971 | Becker |
| 3,595,891 A | 7/1971 | Cavitt |
| 3,953,362 A | 4/1976 | Lines et al. |
| 3,983,028 A | 9/1976 | McCollum et al. |
| 4,022,681 A | 5/1977 | Sheng et al. |
| 4,066,561 A | 1/1978 | Nnadi |
| 4,125,455 A | 11/1978 | Herbstman |
| 4,134,825 A | 1/1979 | Bearden, Jr. et al. |
| 4,151,070 A | 4/1979 | Allan et al. |
| 4,181,601 A | 1/1980 | Sze |
| 4,192,735 A | 3/1980 | Aldridge et al. |
| 4,305,808 A | 12/1981 | Bowes et al. |
| 4,325,802 A | 4/1982 | Porter et al. |
| 4,352,729 A | 10/1982 | Jacquin et al. |
| 4,411,768 A | 10/1983 | Unger et al. |
| 4,422,927 A | 12/1983 | Kowalczyk et al. |
| 4,435,314 A | 3/1984 | van de Leemput et al. |
| 4,454,023 A | 6/1984 | Lutz |
| 4,465,630 A | 8/1984 | Akashi et al. |
| 4,467,049 A | 8/1984 | Yoshii et al. |
| 4,485,004 A | 11/1984 | Fisher et al. |
| 4,581,344 A | 4/1986 | Ledoux et al. |
| 4,585,545 A | 4/1986 | Yancey, Jr. et al. |
| 4,590,172 A | 5/1986 | Isaacs |
| 4,592,827 A | 6/1986 | Galiasso et al. |
| 4,592,830 A | 6/1986 | Howell et al. |
| 4,606,809 A | 8/1986 | Garg |
| 4,633,001 A | 12/1986 | Cells |
| 4,652,311 A | 3/1987 | Gulla et al. |
| 4,652,647 A | 3/1987 | Schlosberg et al. |
| 4,693,991 A | 9/1987 | Bjornson et al. |
| 4,695,369 A | 9/1987 | Garg et al. |
| 4,707,245 A | 11/1987 | Baldasarri et al. |
| 4,707,246 A | 11/1987 | Gardner et al. |
| 4,713,167 A | 12/1987 | Reno et al. |
| 4,716,142 A | 12/1987 | Laine et al. |
| 4,734,186 A | 3/1988 | Parrott et al. |
| 4,762,607 A | 8/1988 | Aldridge et al. |
| 4,762,814 A | 8/1988 | Parrott et al. |
| 4,765,882 A | 8/1988 | Aldridge et al. |
| 4,770,764 A | 9/1988 | Ohtake et al. |
| 4,802,972 A | 2/1989 | Kukes et al. |
| 4,812,228 A | 3/1989 | Angevine et al. |
| 4,824,611 A | 4/1989 | Cells |
| 4,834,865 A | 5/1989 | Kukes et al. |
| 4,837,193 A * | 6/1989 | Akizuki et al. ............... 502/242 |
| 4,863,887 A | 9/1989 | Ohtake et al. |
| 5,017,712 A | 5/1991 | Usui et al. |
| 5,114,900 A | 5/1992 | King |
| 5,171,916 A | 12/1992 | Le et al. |
| 5,254,240 A | 10/1993 | Galiassco et al. |
| 5,332,709 A | 7/1994 | Nappier et al. |
| 5,358,634 A | 10/1994 | Rankel |

(Continued)

FOREIGN PATENT DOCUMENTS

CA    2004882    6/1991

(Continued)

OTHER PUBLICATIONS

Molecular Profile Report, Cobalt Benzoate, http://chemfindercambridgesoft.com/chembiofinder/Forms/Search/ContentArea/ChemBioVizSearch.aspx?FormGroupId=8&AppName=chembiofinder&AllowFullSearch=true&KeepRecordCountSynchronized=false&SearchCriteriald=4&SearchCriteriaValue=932-69-4&CurrentIndex=0.*
Office Action dated Apr. 2, 2009 cited in U.S. Appl. No. 11/327,085.
Papaioannou et al., "Alkali-Metal- and Alkaline-Earth-Promoted Catalysts for Coal Liquefaction Applications", Energy & Fuels, vol. 4, No. 1, pp. 38-42 (1990).
Office Action dated Sep. 30, 2009 cited in U.S. Appl. No. 11/461,652.
Notice of Allowance dated Oct. 27, 2009 cited in U.S. Appl. No. 11/327,085.
Database CA [online] Chemical Abstracts Service retrieved from STN Database accession No. 1991:42412.
Hydrocracking of Liaohe Vacuum Residue With Bimeta:, Shen et al., Preprints of Symposia—American Chemical society, Division of Fuel Chemistry (1998), 43(3), 481-485, OCDEN: Psadfz, 1998, XP009117504.

(Continued)

*Primary Examiner* — Walter D Griffin
*Assistant Examiner* — Renee Robinson
(74) *Attorney, Agent, or Firm* — Workman Nydegger

(57) ABSTRACT

Oil soluble catalysts are used to convert polynuclear aromatic compounds in a hydrocarbon feedstock to higher value mono-aromatic compounds. The catalyst complex includes a catalytic metal center that is bonded to a plurality of organic ligands that make the catalyst complex oil-soluble. The ligands include an aromatic ring and a ligand spacer group. The ligand spacer group provides spacing of 2-6 atoms between the metal center and the aromatic ring. The spacing between the aromatic group and the catalytic metal center advantageously allows the catalyst to selectively crack polynuclear aromatic rings while preserving one of the aromatic rings, thereby increasing the content of mono-aromatic compounds in the hydrocarbon feedstock.

25 Claims, No Drawings

U.S. PATENT DOCUMENTS

| | | | |
|---|---|---|---|
| 5,364,524 | A | 11/1994 | Partridge et al. |
| 5,372,705 | A | 12/1994 | Bhattacharya et al. |
| 5,474,977 | A | 12/1995 | Gatsis |
| 5,578,197 | A | 11/1996 | Cyr et al. |
| 5,622,616 | A | 4/1997 | Porter et al. |
| 5,866,501 | A | 2/1999 | Pradhan et al. |
| 5,868,923 | A | 2/1999 | Porter et al. |
| 5,871,638 | A | 2/1999 | Pradhan et al. |
| 5,916,432 | A | 6/1999 | McFarlane et al. |
| 5,935,419 | A | 8/1999 | Khan et al. |
| 5,954,945 | A | 9/1999 | Cayton et al. |
| 5,962,364 | A | 10/1999 | Wilson, Jr. et al. |
| 6,059,957 | A | 5/2000 | Khan et al. |
| 6,068,758 | A | 5/2000 | Strausz |
| 6,093,824 | A | 7/2000 | Reichle et al. |
| 6,136,179 | A | 10/2000 | Sherwood, Jr. et al. |
| 6,139,723 | A | 10/2000 | Pelrine et al. |
| 6,214,195 | B1 | 4/2001 | Yadav et al. |
| 6,274,530 | B1 | 8/2001 | Cayton et al. |
| 6,379,532 | B1 | 4/2002 | Hoehn et al. |
| 6,455,594 | B1 | 9/2002 | Tsuji |
| 6,462,095 | B1 | 10/2002 | Bonsel et al. |
| 6,596,155 | B1 | 7/2003 | Gates et al. |
| 6,660,157 | B2 | 12/2003 | Que et al. |
| 6,686,308 | B2 | 2/2004 | Mao et al. |
| 6,712,955 | B1 | 3/2004 | Hou et al. |
| 6,884,340 | B1 | 4/2005 | Bogdan |
| 6,916,762 | B2 | 7/2005 | Shibuya et al. |
| 7,011,807 | B2 | 3/2006 | Zhou et al. |
| 7,090,767 | B2 | 8/2006 | Kaminsky et al. |
| 2002/0179493 | A1 | 12/2002 | Etter |
| 2003/0094400 | A1 | 5/2003 | Levy et al. |
| 2003/0171207 | A1 | 9/2003 | Shih et al. |
| 2004/0147618 | A1 | 7/2004 | Lee et al. |
| 2005/0109674 | A1 | 5/2005 | Klein |
| 2005/0241991 | A1 | 11/2005 | Lott et al. |
| 2005/0241992 | A1 | 11/2005 | Lott et al. |
| 2005/0241993 | A1 | 11/2005 | Lott et al. |
| 2005/0258073 | A1 | 11/2005 | Oballa et al. |
| 2005/0279670 | A1 | 12/2005 | Long et al. |
| 2006/0079396 | A1 | 4/2006 | Saito |
| 2006/0224000 | A1 | 10/2006 | Papp et al. |
| 2006/0254956 | A1 | 11/2006 | Khan |
| 2006/0289340 | A1 | 12/2006 | Brownscombe et al. |
| 2007/0012595 | A1 | 1/2007 | Brownscombe et al. |
| 2007/0090018 | A1 | 4/2007 | Keusenkothen et al. |
| 2007/0158236 | A1 | 7/2007 | Zhou et al. |
| 2007/0158238 | A1 | 7/2007 | Wu et al. |
| 2007/0163921 | A1 | 7/2007 | Keusenkothen et al. |
| 2007/0175797 | A1 | 8/2007 | Iki et al. |
| 2007/0209965 | A1 | 9/2007 | Duddy et al. |

FOREIGN PATENT DOCUMENTS

| | | |
|---|---|---|
| CA | 2088402 | 7/1993 |
| DE | 2324441 | 12/1973 |
| DE | 2421934 | 11/1974 |
| EP | 0 199 399 | 10/1986 |
| EP | 0559399 | 9/1993 |
| EP | 1043069 | 10/2000 |
| JP | 06346064 | 12/1994 |
| JP | 2003193074 | 7/2003 |
| WO | WO2006116913 | 11/2006 |

OTHER PUBLICATIONS

Office Action dated Mar. 8, 2010 cited in U.S. Appl. No. 11/461,652.
Notice of Allowance dated Aug. 5, 2010 cited in U.S. Appl. No. 11/461,652.
Office Action dated Sep. 20, 2010 cited in U.S. Appl. No. 11/968,934.
Office Action dated Jan. 25, 2011 cited in U.S. Appl. No. 11/968,934.

* cited by examiner

CATALYST FOR HYDROCRACKING HYDROCARBONS CONTAINING POLYNUCLEAR AROMATIC COMPOUNDS

BACKGROUND OF THE INVENTION

1. The Field of the Invention

The present invention relates generally to the manufacture of catalyst for catalytically cracking hydrocarbons that have polynuclear aromatic compounds (e.g., cycle oil).

2. The Related Technology

Effective techniques for manufacturing the greatest amount of high quality products from low quality crudes are needed for the economic viability of the petroleum refining industry. Because crude oils are obtained from the ground, they can have widely varying types and amounts of hydrocarbons and impurities. Distillation of crude oils produces large fractions of hydrocarbons that are not very useful as fuels or other higher end uses. For decades, the refining industry has been intensively researching ways to economically convert these fractions into products that are more valuable. There are now many refining techniques that economically convert unusable fractions into higher value petroleum products.

Ideally all the hydrocarbons in a barrel of oil would be upgraded to high-value, useable products. However, despite the industry's extensive research there are certain distillates, and/or by-products of the various refining processes that are difficult to upgrade. Difficult-to-upgrade hydrocarbons include the distillation tower resids; pyrolysis fuel oil, which is a by-product of steam cracking to make olefins; and cycle oil, which is a by-product of fluidized catalytic crackers that are used extensively to produce gasoline stocks.

These hydrocarbons can be difficult to upgrade because they often contain impurities such as sulfur and heavy metals and/or significant quantities of very high molecular weight hydrocarbons, polynuclear aromatics, and asphaltenes. Hydrocarbons containing these types of hydrocarbons tend to form coke under hydrocracking conditions, which can foul reactors and reduce the yield of the hydrocracking process. Consequently, these products are typically used "as is" in their low-value form.

Because pyrolysis fuel oil and cycle oil are a byproduct of other refining processes, these products are necessarily produced in most refineries and must be dealt with. The traditional approach has been to sell PFO and cycle oil as a fuel to be burned in power generation. PFO and cycle oils have a foul smell, are toxic, and produce pollution when burned. Environmental agencies have for years regulated the disposal and burning of PFO and cycle oils. These oils typically must be blended with other fuel oils, such as "bunker oils," to pass regulatory restrictions when burned. The restrictions make it even more difficult to use these materials as fuels and have suppressed the price that industry is willing to pay for them. Despite the continuing pressures to catalytically upgrade hydrocarbons such as PFO and cycle oil, thereby creating a long-felt but unsatisfied need, an economical process has thus far eluded the industry.

BRIEF SUMMARY OF THE INVENTION

The present invention relates to an oil soluble catalyst for upgrading hydrocarbon feedstocks that contain polynuclear aromatic compounds. The catalysts of the invention can be used to convert the polynuclear aromatic compounds to higher value mono-aromatic compounds. The catalyst complex includes a catalytic metal center that is bonded to a plurality of organic ligands that render the catalyst complex oil-soluble. The ligands include an aromatic ring and a ligand spacer group. The ligand spacer group provides spacing of 2-6 atoms between the metal center and the aromatic ring. The spacing between the aromatic group and the catalytic metal center advantageously allows the catalyst to selectively crack polynuclear aromatic rings while preserving one of the aromatic rings, thereby increasing the content of mono-aromatic compounds in the hydrocarbon material.

The active metals included in the catalysts of the invention are metals that are useful for cracking polyaromatic compounds found in heavy crude oils, resids, pyrolysis fuel oil, cycle oils, and similar hydrocarbons. In one embodiment the catalytic metal atom can be a group VIB metal, a group VIIIB metal or a combination of these. Examples of suitable catalytic metals include tungsten, molybdenum, chromium, nickel, cobalt, iron, vanadium, titanium, manganese, and combinations of these.

The ligand bonded to the metal atom includes an aromatic group that can form pi-pi ($\pi$-$\pi$) stacking interactions with polynuclear aromatic compounds in the hydrocarbon feedstocks. The aromatic group of the ligand is typically a substituted or unsubstituted five or six member aromatic ring (e.g., aryl group). The aromatic group can also be alkylated or functionalized in other ways to provide desired steric hinderances and/or bonding interactions with other ligands or molecules in the hydrocarbon feedstock, so long as the ligands remain oil soluble. In a preferred embodiment, the aromatic group of the ligand is monocyclic.

The aromatic ring of the ligand is separated from the metal by a ligand spacer group. The ligand spacer group can be any group that can be bonded to the aromatic ring and to the catalytic metal and can provide spacing of 2-6 atoms between the metal atom and the aromatic ring of the ligand. In one embodiment, the catalyst can have the following structure:

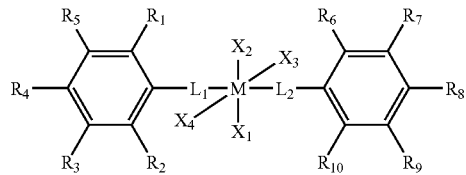

In the foregoing structure, M can be an VIII B metal, a VI B metal, a base transition metal, or a combination thereof; $L_1$ and $L_2$ are ligand spacer groups with a first atom bonded to the aromatic group and a second atom bonded to the metal and providing a spacing of 2-6 atoms between the aromatic group and the metal; $R_1$-$R_{10}$ are independently a hydrogen, an alkyl group, or a bond to a ligand of another metal-ligand complex; $X_1$-$X_4$ are optional ligands to the catalytic metal.

The spacing between the aromatic ring and the metal atom provides a molecular template that acts to control the catalytic hydrocracking process so as to selectively crack polynuclear aromatic compounds into higher value mono-aromatic compounds. Mono-aromatic compounds are produced from the catalyst template because one aromatic ring of the polynuclear aromatic compound interacts with the aromatic ring of the catalyst and the other ring(s) of the polynuclear aromatic compound is/are positioned near the catalytic metal. The spacer group provides the proper spacing for the metal atom to crack the aromatic rings of the polynuclear aromatic compound that are not bonded to the aromatic ring of the ligand. By providing a spacing of at least two atoms between the metal and the aromatic group of the ligand, the metal atom is prevented from cracking the one aromatic ring that is bonded to the catalyst. In this way, the catalyst selectively cracks one or more of the aromatic rings of the polynuclear aromatic compounds while preserving one of the rings, thereby forming a mono-aromatic compound.

Because of the longstanding need to dispose of hard-to-upgrade hydrocarbons, there have been many attempts in the prior art to crack these products. Many of these methods have used catalysts that crack the polynuclear aromatics in a non-specific manner to form alkanes such as diesel and gasoline. However, these processes have yet to be shown to be economically viable. In contrast, the catalyst of the present invention can unexpectedly crack the polynuclear aromatics in a controlled and selective manner to produce a significant fraction of higher value mono-aromatic compounds (e.g., BTX products), thereby increasing the economic viability of the process. Importantly, the catalyst can produce the mono-aromatic compounds directly from the polynuclear aromatic compounds during the cracking process. Mono-aromatic compounds such as BTX have higher commercial value compared to diesel and gasoline, which are composed largely of non-aromatic alkanes.

DETAILED DESCRIPTION OF EXAMPLE EMBODIMENTS

I. Introduction and Definitions

The present invention is directed to a catalyst for hydrocracking hydrocarbon materials that contain polynuclear aromatic compounds. The catalyst can be used in a hydrocracking process to increase the monoaromatic content (e.g., BTX content) of the hydrocarbon material.

For purposes of this invention, the term "acid residue" is the portion of an acid molecule that persists after the acid has been reacted with another molecule. The acid residue therefore differs from its acid molecule by the loss of an atom (e.g., a hydrogen) resulting from the reaction of the acid with another molecule. For example, an ester group and a metal carboxylate are examples of acid residues of a compound containing a carboxylic acid.

For purposes of this invention, the term "substantially free of Ramsbottom carbon residue" means a Ramsbottom carbon content of less than 1.0% as determined according to ASTM D524.

The term "BTX" refers to benzene, toluene, xylene and ethyl benzene.

For purposes of this invention, the term "refining by-product" is a hydrocarbon product obtained from refining a petroleum distillate where the "refining by-product" is lower in value and produced in lower quantities than at least one other hydrocarbon product produced during the same refining process.

II. Components Used to Make Oil Soluble Catalyst

The catalysts of the invention include a plurality of catalyst complexes, which include a catalytic metal center and a plurality of organic ligands. Optionally, the catalyst complexes can be dispersed in a solvent or carrier. The following components can be used to manufacture the catalysts of the invention.

A. Catalytic Metals

The catalytic metal is a transition metal selected for its ability to form a bond with the organic ligand and to catalytically crack aromatic rings of polynuclear aromatic compounds under hydrocracking conditions. In one embodiment, the catalytic metals are selected from groups VIB and VIIIB of the Periodic Table. Examples of suitable metals include, but are not limited to, tungsten (W), molybdenum (Mo), chromium (Cr), nickel (Ni), cobalt (Co), iron (Fe), vanadium (V), titanium (Ti), and manganese (Mn).

The catalyst atoms may be provided in the form of metal hydroxide, metal chloride, metal sulfate, metal nitrate, metal oxide, or other metal salts. For example, where molybdenum is used, examples of suitable molybdenum compounds include molybdenum halides such as molybdenum hexafluoride and molybdenum pentachloride, the various oxides of molybdenum such as molybdenum dioxide, trioxide and sesquioxide, and the like; alkali and alkali earth molybdates such as cesium molybdate, sodium molybdate, potassium molybdate, calcium molybdate and the like; and ammonium molybdate or molybdic acid. Examples of other suitable metal compounds include cobalt (II) hydroxide, nickel (II) hydroxide, hydrated iron (III) oxide (FeO(OH)), manganese (II) oxide, $FeCl_3$, $Fe(NO_3)_3$, and $Fe_2(SO_4)_3$.

The catalytic metals can be used alone or in combination. In one embodiment, at least Mo is used as a primary metal component and optionally in combination with at least one other base transition metal. The use of Mo in combination with at least one other base transition metal has been shown to provide superior results compared to Mo alone or the base transition alone.

B. Aromatic Ligands

The aromatic ligands are organic compounds that can form a complex with the catalytic metals. The aromatic ligands include an aromatic group and a ligand spacer group. The ligand spacer group is attached to the aromatic group and provides the bonding interaction with the catalytic metal. The aromatic ligands can have any aromatic group and any substituents bonded thereto so long as the aromatic ligand is capable of being bonded to the catalytic metal through the ligand spacer group and the complex that includes the ligand can be oil soluble. The aromatic ring can be bicyclic or monocyclic. Monocyclic aromatic rings are preferred for their ability to pi-stack with one aromatic ring in the polynuclear aromatic compounds to be hydrocracked. In one embodiment, the aromatic group is a five or six member aromatic ring. The ring structure of the aromatic group can be all carbons or can include heteroatoms (e.g., nitrogen or oxygen). The aromatic ring can also include substituents. In one embodiment, the aromatic ring includes alkyl substituents, which can provide added solubility in oil. These alkyl groups can be straight-chain or branched and typically have between 1 and 18 carbon atoms, more preferably between 2 and 12 carbon atoms, and most preferably between 3 and 8 carbons.

The aromatic ligands include a ligand spacing group. The ligand spacing group includes a chain of atoms that are bonded or can be bonded at the ends to the aromatic group and the catalytic metal to provide spacing of 2-6 atoms between the aromatic group and the catalytic metal. More preferably the ligand spacing group includes a chain of atoms that provide spacing of 2-4 atoms.

The ligand spacing group of the aromatic ligand includes at least one functional group that can form a bond with the catalytic metal. In one embodiment, the available functional group on the aromatic ligand is an acid group. Examples of suitable acid groups include carboxylic acids, phosphonic acids, sulfonic acids, boric acids, nitric acid, and derivatives thereof.

Examples of suitable aromatic acids that can be used as an organic ligand include compounds that contain one ring or two fused rings and contain from 6-14 atoms. Examples include benzene carboxylic acid, naphthalene carboxylic acid, methylbenzoic acid, ethyl phenyl acetic acid, and the like. Single rings are preferred for their selective production of mono-aromatics in the hydrocracking process.

Optionally, the ligand spacing group includes one or more side groups that extend from the main chain of 2-6 atoms linking the catalytic metal to the aromatic ring. The side groups can provide oil solubility and/or electric or steric hindrances between the catalytic metal and the polynuclear aromatics that are bonded to the aromatic ligand through pi-pi stacking interactions.

In one embodiment, the aromatic ligand is provided as a single molecule that includes both the aromatic ring and the ligand spacing group in a single molecule. Alternatively, the aromatic ligand can be provided by reacting an aromatic compound with a ligand spacer molecule which, once attached to the aromatic compound and the metal atom, serves as the ligand spacer group. The ligand spacer molecule includes a first functional group capable of reacting with the catalytic metal as described above. The ligand spacer molecule also includes a second functional group capable of reacting with an aromatic compound.

The linkage between the ligand spacer molecule and the aromatic compound will depend on the functional groups available on the aromatic compound. Any suitable linkage known in the art can be used. Examples of suitable functional groups include hydroxyl, carboxyl, carbonyl, amine, amide, nitrile, thiol, a sulfonic acid, etc. For example, in one embodiment, the aromatic compound can include a hydroxyl group that can react with an acid group of a ligand spacing molecule to form an ester linkage.

One type of molecule that can be used as a ligand spacer molecule is a diacid and/or a diprotic acid. Examples of suitable acid groups include carboxylic acids, phosphonic acids, sulfonic acids, boric acids and derivatives thereof. Examples of specific compounds include oxalic acid, oxamic acid, malonic acid, succinic acid, glutaric acid, propylphosphonic acid, tert-Butylphosphonic acid, 3-(Methylphosphinico)propionic acid, dibutyl phosphate, bis(2-ethylhexyl) phosphate, sulfoacetic acid, methylboronic acid, isopropylboronic acid, butylboronic acid, isobutylboronic acid and their derivatives.

In some cases, the aromatic ligand can function as a solvent for the reaction to make the catalyst complexes. This is typically the case where the aromatic ligand is a liquid under the reaction conditions. However, if needed, other solvents can be used. The additional solvent should dissolve the aromatic ligands and the catalytic metal compounds and not interfere with the reaction between them. Suitable solvents include benzene, toluene, xylene, ethyl benzene, naphtha, mineral oil, mineral spirits, combinations thereof, and the like.

C. Reducing Agents

Optionally, a reducing agent can be added to the reaction mixture during the formation of the catalyst complexes to cause the metal atoms and ligands to more readily form a complex and/or to obtain metal complexes with a desired number of ligands. The use of a reducing agent has been found to be particularly useful for the formation of complexes with molybdenum atoms in combination with an acid bearing ligand. In one embodiment, the reducing agent can also be used to maintain at least a portion of the molybdenum atoms in an oxidation state below 4+.

Any reducing agent that can reduce the catalytic metal atoms can be used. In a preferred embodiment, the reducing agent is a strong reducing agent under the reaction conditions described herein. Suitable reducing agents include methane, ethane, olefins such as ethylene and propylene, aldehydes such as formaldehyde, and hydrogen. Hydrogen gas is a particularly preferred reducing agent for its strong reducing potential.

The suitability of the reducing agent often depends on the temperature at which the reaction is performed. At higher temperatures (e.g., 150° C.), organic reducing agents such as methane and formaldehyde have suitable reducing potential. However, at low temperatures (e.g., below 50° C.) or room temperature it can be advantageous to use a stronger reducing agent such as hydrogen gas.

III. Methods of Making Hydrocracking Catalyst

The process for making the hydrocracking catalysts according to the present invention can be carried out by reacting a plurality of aromatic ligand molecules with a plurality of catalytic metal atoms. An aromatic ligand that includes a ligand spacer group capable of bonding with the catalytic metal atoms is mixed together with the catalytic metal and optionally one or more solvents to form a mixture. The catalytic atoms are allowed to react with the functional group available on the ligand spacer group to form a metal ligand complex. The optimal reaction temperature for carrying out this reaction will depend on the particular catalytic metal and organic ligand. In one embodiment, the temperature for reacting the catalytic metal (e.g., with benzene carboxylic acid) is typically in a range from about 100 to about 300° C., more preferably about 150 to about 250° C.

In one embodiment, the aromatic ligand is not provided as a single molecule having an aromatic ring and a ligand spacer group. Instead, a ligand spacer molecule and an aromatic ring compound can be provided separately and reacted together to form the aromatic ligand. The ligand spacer molecule can be reacted with an aromatic compound before, after, or simultaneously with the reaction with the catalytic metal.

The use of a ligand spacer molecule can be advantageous for obtaining good yields of certain metals (e.g., base transition metals such as nickel) which can be more difficult to react directly with some organic ligand compounds. In addition, the use of a ligand spacer molecule is advantageous where it is desired to provide side chains that extend from the ligand spacer group. By providing the ligand spacer group separately from the aromatic compound, the side chain groups can be selected independently from the aromatic compound. This feature allows greater flexibility in providing the desired solubility and steric effects of the side chains.

In one embodiment, the catalyst of the invention includes at least two different catalytic metals. The bimetallic or multimetallic catalysts can be manufactured by making separate catalyst complexes using a single metal and then combining the complexes to form the bimetallic or multimetallic catalysts. Any combination of metals can be used; however, the combination of molybdenum and another base transition metal has been found to be particularly useful for hydrocracking pyrolysis fuel oil and/or cycle oils. In one embodiment, the ratio of the first metal (e.g., molybdenum) to the second metal (e.g., nickel) is in a range from about 50:1 to about 1:20, more preferably about 10:1 to about 1:5, and most preferably in a range from about 6:1 to about 1:2. The first and second catalytic metals can be complexed using the same or different aromatic ligands.

In one embodiment of the invention, the reaction of the catalytic metal with the aromatic ligand is carried out in the presence of a reducing agent. The use of a reducing agent can produce a catalyst with the catalytic metal in a lower oxidation state and thereby reduce the amount of aromatic ligands per catalytic metal. In addition, the use of a reducing agent can improve the solubility of the catalyst in PFO and cycle oil. In a preferred embodiment, the reducing agent used is hydrogen.

IV. Oil Soluble Catalyst

The methods of the present invention can be used to manufacture an oil soluble catalyst that is useful for upgrading polynuclear aromatics to mono-aromatic compounds. In one embodiment, the catalyst complexes have the following structure:

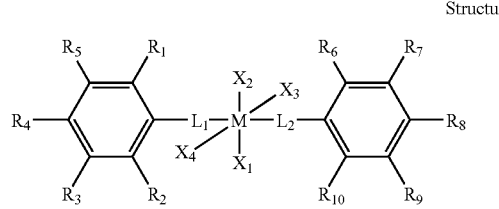

Structure 1

In the foregoing structure, M can be a group VIB metal, a group VIIIB metal, a base transition metal, or a combination of these, more preferably M is W, Mo, Cr, Ni, Co, Fe, V, Ti, Mn, or a combination of these; $L_1$ and $L_2$ are ligand spacer groups with a first atom bonded to the aromatic group and a second atom bonded to the metal and providing a spacing of 2-6 atoms between the aromatic group and the metal; $R_1$-$R_{10}$ are independently a hydrogen, an alkyl group, or a bond to a ligand spacer group that is bonded to another metal-atom; $X_1$-$X_4$ are optional ligands bonded to the catalytic metal (e.g., which can form an extended network for intercomplexed ligands and metal atoms, e.g., structure 3 below).

In an alternative embodiment, the catalyst can have the following structure:

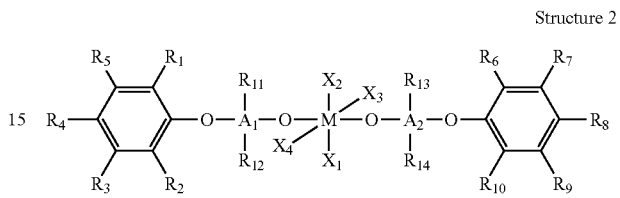

Structure 2

In structure 2, M, $R_1$-$R_{10}$, and $X_1$-$X_4$ are the same as in Structure 1. $A_1$ and $A_2$ comprise a single atom or a chain of atoms, at least one of the atoms is selected from the group consisting of B, N, P, S, or C; and $R_{11}$-$R_{14}$ are independently a single bonded oxygen, a double bonded oxygen, or an alkoxide.

An exemplary extended network of intercomplexed ligands and metal atoms is shown below in the following structure:

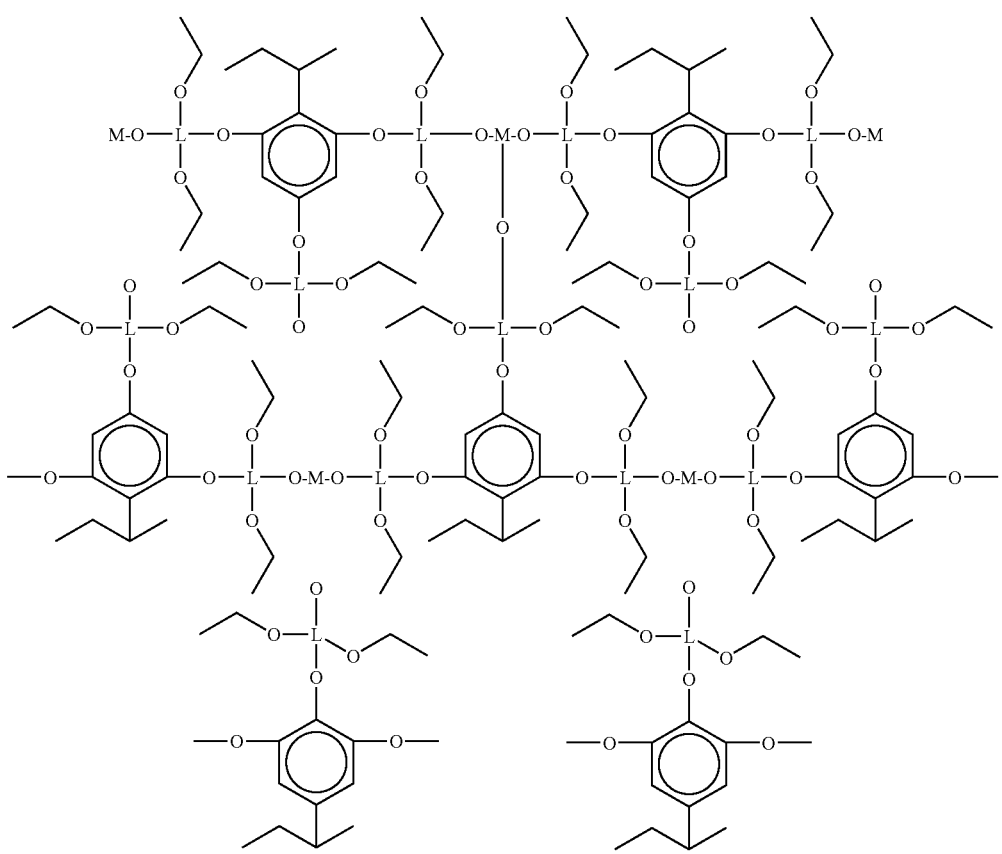

Structure 3

In structure 3, M is a metal such as W, Mo, Ni, Co, Fe, Group VIB metal, or Group VIIIB metal, L can be C, B, N, P, or S.

In one embodiment, the oil soluble catalyst is a mixture of two or more complexes with different metals. Mixtures of Mo or tungsten complexes with Ni, Co, and/or Fe have been found to work surprisingly well for cracking polynuclear aromatic compounds. In one embodiment, the oil soluble catalyst includes a Mo complex and a complex that includes Ni, Co, and/or Fe in a ratio of 50:1 to 1:20, more preferably 10:1 to 1:5. Preferred organic ligands for the molybdenum complexes include aromatic carboxylic acids where the carboxylic acid serves as the ligand spacer group. Preferred ligand spacer groups for the Ni, Co, and/or Fe include carboxylic acids, phosphonic acids, sulfonic acids, boric acids and derivatives thereof.

V. Methods for Upgrading Polyaromatic Hydrocarbons

The catalysts of the present invention can be used to increase the monoaromatic content of hydrocarbon materials by converting polynuclear aromatic hydrocarbons to monoaromatic hydrocarbons. The method includes providing a hydrocarbon material, blending the catalyst complexes of the invention into the hydrocarbon material, and processing the hydrocarbon material under hydrocracking conditions to increase the percentage of monoaromatic compounds while decreasing the percentage of polynuclear aromatics.

A. Providing Hydrocarbon Material

The catalyst can be used with any hydrocarbon material that includes significant quantities of polynuclear aromatic hydrocarbons. Examples of suitable types of hydrocarbon materials include cycle oils, including heaving cycle oils, pyrolysis fuel oils, FCC slurry oils, bunker oil, resids, and crude oils that contain polynuclear aromatics. Examples of the types of polynuclear aromatic hydrocarbons that can be hyrdocracked using the catalyst of the invention include, anthracene, benzopyrene, chrysene, coronene, corannulene, naphtacene, naphthalene, pentacene, phenanthrene, pyrene, triphenylene, and ovalene.

The hydrocarbon material can include polynuclear aromatics in a range from about 0.1% to about 99%, more preferably, in a range from about 10% to about 75%, and most preferably in a range from about 20% to about 60%. In one embodiment, the foregoing ranges for concentrations of polynuclear aromatics are for hydrocarbons that boil at less than about 1000° F. The present invention has been found to work surprisingly well with these types of hydrocarbons. In one embodiment, the feedstock has less than about 50 wt % hydrocarbons boiling above about 1000° F., more preferably less than about 25 wt %, and most preferably less than about 10 wt %. Alternatively, the hydrocarbon feedstock can be selected according to the wt % of hydrocarbons boiling in a range from about 350° F. to about 1000° F. In one embodiment, the hydrocarbon feedstock contains at least 50 wt % hydrocarbons boiling between about 350° F. and about 1000° F., more preferably at least about 70 wt % and most preferably at least about 90 wt %. While these materials have been found to be particularly suited for the process of the present invention, the invention is not limited to these hydrocarbon materials.

In one embodiment of the invention, the hydrocarbon feedstock is a by-product of a petroleum refining process (i.e., a by-product from refining a distilled fraction of a crude oil). Examples of refining by-products include cycle oils and pyrolysis fuel oils.

The catalyst of the present invention has been found to work surprisingly well to upgrade cycle oil, particularly heavy cycle oils. Cycle oils are a byproduct of fluid catalytic cracking. Cycle oils are oily hydrocarbons that have very low Ramsbottom carbon residue (in one embodiment the cycle oils are substantially free of Ramsbottom carbon residue) and have little to no heavies boiling over 950° F. In one embodiment, the carbon residue is less than 1.0 wt %, more preferably less than about 0.9 wt %, and most preferably less than about 0.8 wt % and the amount of heavies boiling above 950° F. is less than about 10 wt %, more preferably less than about 5 wt %, and most preferably less than about 2 wt %. Yet, cycle oils are difficult to upgrade because they contain significant quantities of polynuclear aromatic compounds. The relatively high polynuclear aromatic content and relatively low to non-existent content of Ramsbottom carbon residue and heavies has been found to be uniquely suited for use with the catalyst of the invention to produce mono-aromatic compounds.

Another type of refining by-product particularly suited for use with the catalyst of the invention is pyrolysis fuel oil, and particularly the heavy fraction of pyrolysis fuel oil. Pyrolysis fuel oil is a byproduct of steam cracking of naphtha and ethane to form olefins. Because of the complicated nature of the hydrocarbons in pyrolysis fuel oil, pyrolysis fuel oil is typically characterized by its source rather than the exact components that comprise this material. While the exact contents of pyrolysis oil can vary, pyrolysis fuel oil usually has significant quantities of polynuclear aromatic compounds. Pyrolysis fuel oil has been found to be a surprisingly good hydrocarbon source to derive a benefit from the catalyst of the present invention.

In one embodiment, the hydrocarbon feedstock used in the invention has between about 10 wt % and 90 wt % polynuclear aromatics, more preferably between 20% and 80%. Another way of determining the suitability of the hydrocarbon feedstock for use in the present invention is evaluating the percent of hydrocarbons boiling above 950° F. In one embodiment, the feedstock includes less than 50 wt % of hydrocarbons boiling above 950° F., more preferably less than 25 wt % and most preferably less than 10%. In one embodiment the foregoing weight percents can be for a boiling range of between 650° F. and 950° F.

The hydrocarbon feedstock can also be a blend of different hydrocarbons from different sources. In a preferred embodiment, the hydrocarbon feedstock contains at least about 20 wt % of a refining by-product, more preferably at least about 50 wt %, even more preferably at least about 75 wt %, even more preferably yet at least 90 wt %, and most preferably substantially all of the hydrocarbon feedstock used in the process is a by-product of a refining process obtained downstream from distillation.

B. Blending the Catalyst Complex with the Hydrocarbon Material

The catalyst complex comprising the aromatic ligand and catalytic metal is blended into the polyaromatic-containing hydrocarbon feedstock. The catalyst can be blended directly into the feedstock or the catalyst can be diluted in one or more subsequent steps. The step-wise dilution can facilitate intimate mixing of the catalyst and the hydrocarbon. The hydrocarbon used to carry out dilution can be the same material to be hydrocracked, or alternatively, a different hydrocarbon can be used as the diluent. Examples of suitable diluents include vacuum gas oil, decant oil, or light gas oil. Suitable solvents include benzene, toluene, xylene, ethyl benzene, naphtha, mineral oil, mineral spirits, combinations thereof, and the like.

It has been found that pre-blending the precursor composition with a hydrocarbon diluent prior to blending the diluted precursor mixture with the feedstock greatly aids in thoroughly and intimately blending the catalyst complex within the feedstock, particularly in the relatively short period of time required for large-scale industrial operations to be economically viable. In one embodiment the catalyst is blended with the diluent for a period of time in a range of about ½ minute to about 20 minutes, more preferably in a range from about 1 minute to about 10 minutes, and most preferably in a range of about 2 minutes to about 5 minutes. Increasing the vigorousness and/or shearing energy of the mixing process generally reduce the time required to effect thorough mixing.

The catalyst or the diluted catalyst is blended with the hydrocarbon feedstock to achieve a desired metal concentration. In one embodiment, the concentration of the catalyst in the feedstock is in a range from about 1 ppm to about 1,000 ppm, more preferably 10 ppm to about 750 ppm, and most preferably 50 ppm to about 500 ppm.

C. Hydrocracking Polynuclear Aromatics to Mono-Aromatics

The hydrocarbon feedstock is reacted with hydrogen in the presence of the catalyst of the invention under hydrocracking conditions so as to increase the mono-aromatic content while reducing the polynuclear aromatic content in the feedstock.

The hydrocracking process can be carried out in any reactor so long as intimate contact can be maintained between the catalyst, the hydrocarbon feedstock, and the free hydrogen gas stream throughout the hydrocracking process. The reactor can be a continuous reactor, semi-continuous reactor, or a batch reactor. The compositions can be pre-mixed before entering the reactor or mixed within the reactor. The reactor can be equipped with a mechanical stirrer or a static mixer or a recirculating pump. In a preferred embodiment, the reactor is a continuous stream reaction vessel with a recirculating pump. Continuous reaction vessels have been found to work well due to the homogeneous nature of the catalyst.

The reaction temperature is selected to promote the conversion of polynuclear aromatics to mono-aromatics. The particular temperature for a given reaction can depend on the hydrocarbon feedstock being used and the decomposition temperature of the catalyst. In general, the hydrocracking temperature can be in a range from about 450° F. to about 1000° F. or higher. Lower temperatures within the range are typically preferred to hinder decomposition of the catalyst. In a preferred embodiment, the hydrocracking temperature is less than about 950° F., more preferably less than 500° F.

Any suitable pressure can be used in the hydrocracking process of the invention. The reaction pressure can range from about atmospheric pressure to about 10,000 psig. Preferably the pressure is in a range from about 1,000 to about 3,000 psi.

Any suitable amount of hydrogen can be used in the hydrocracking process of the invention. In general the hydrogen flow can be in a range from about 100 to about 20,000 cubic feet of hydrogen per barrel (SCFB). In a preferred embodiment, hydrogen flow is in a range from about 200 to about 2,000 scfb The reaction time is selected to ensure at least partial conversion of the polynuclear aromatics to mono-aromatics. In one embodiment, the reaction time is in a range from about 0.1 to about 10 hour, more preferably in a range from 1 to about 6 hour. For purposes of this invention, when using a continuous flow reactor, the reaction time is the residence time.

During the hydrocracking process of the invention at least a portion of the polynuclear aromatics are converted to mono-aromatic compounds. The catalyst, hydrocarbon feedstock, and hydrocracking conditions are selected to increase the mono-aromatic content in the product and optionally increasing the diesel/gasoline fraction while decreasing the amount of VGO and/or resid and minimize the production of light ends ($C_1$-$C_7$). In one embodiment, the increase in wt % of monoaromatic compounds (e.g., BTX) in the product is in a range from about 10 to about 80, more preferably about 20 to about 60.

The mono-aromatic compounds produced from hydrocracking the polynuclear aromatics according to the process of the invention typically produces mono-aromatic compounds that are substituted with straight chain and/or branched alkyl groups. In one embodiment, this fuel product can be used as is and/or blended with other fuels (e.g., diesel or gasoline). In one embodiment, the product of the hydrocracking process of the invention can be blended with a #2 fuel oil and combusted. Alternatively the cracked product can be blended with a #2 fuel oil and then further refined using traditional refining techniques.

In yet another alternative embodiment, the cracked product is further refined to convert the substituted mono-aromatics to a BTX product or to remove double bonds (i.e., partially or fully saturated hydrocarbon). The BTX or other cyclic hydrocarbon can then be separated from the diesel and/or gasoline fraction. The conversion of substituted mono-aromatics to BTX or cyclic compounds can be carried out using known hydroprocessing techniques. The BTX or cyclic hydrocarbons can be separated from other hydrocarbons in the mixture using liquid-liquid extraction or another suitable separation technique.

In one embodiment, the method of the present invention includes determining the mono-aromatic content of the upgraded product and/or determining the amount by which the aromatic content in the feedstock has increased during the upgrading process. The determination can be made by measuring the actual mono-aromatic content of the upgraded product. Alternatively the determination can be made by selecting a feedstock mixture and hydrocracking conditions that, through prior runs, is known to increase the monoaromatic content within a desired range. This determination can be beneficial as it can provide a basis for determining the added value of the upgrading process and/or can be used to determine the efficiency of the overall upgrading process of the invention. Moreover, by knowing the amount by which the process increases mono-aromatic content, the process can be optimized at least in part on the production of mono-aromatics.

VI. Examples

The following examples provide formulas for making catalyst complexes according to the present invention and for using the catalyst complexes to upgrade hydrocarbon feedstocks that contain polynuclear aromatics.

Example 1

Preparation of Ni Catalyst

Example 1 describes the preparation of an oil soluble nickel complex according to one embodiment of the invention. 108.49 g of dibutyl phosphate (Aldrich, Cat #34810) was placed into a 500 ml round flask and 16 g of Nickel (II) hydroxide ($Ni(OH)_2$, STREM, Cat #93-2847) was added to the dibutyl phosphate. 83.97 g of melted benzene carboxylic acid (ACROS Cat #130375000) was mixed with the nickel and dibutyl phosphate.

This mixture was heated in an oil bath at 130° C. with continuous stirring. The mixture was then heated to a temperature of 180~200° C. and held at this temperature until no water was observed in the distillate. The temperature of the water bath was then quickly decreased to 160° C. and held at this temperature for 1-2 hours until the inside mixture become transparent. The green color solution was then weighed and its metal concentration calculated. The content of nickel in this solution was 4.82 wt %. The following compounds are examples of products that can be produced in the foregoing process:

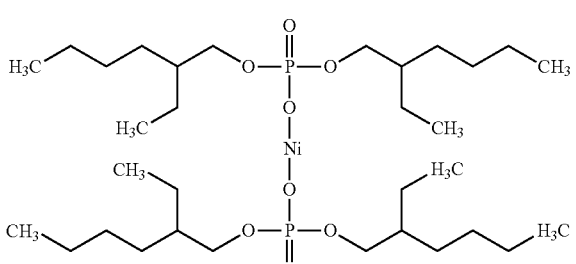

(1)

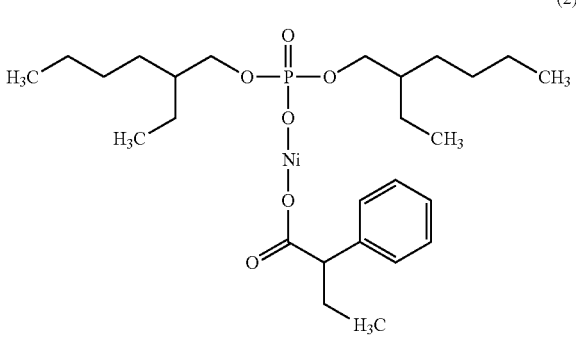

(2)

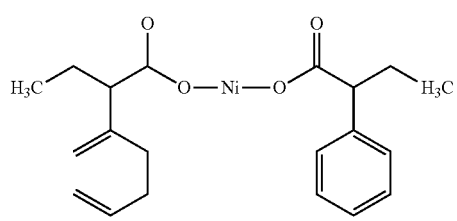

(3)

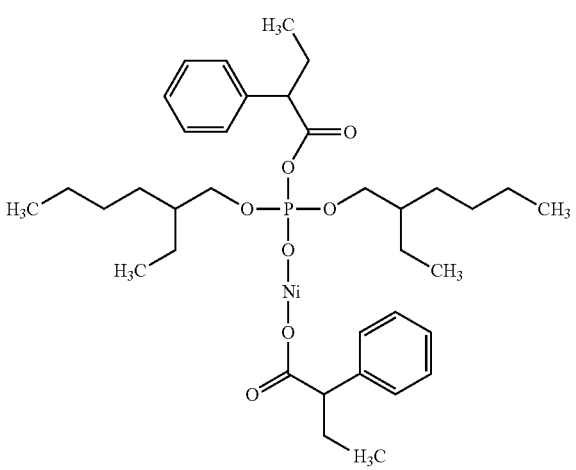

(4)

Example 2

Preparation of Mo Catalyst

Example 2 describes the preparation of an oil soluble molybdenum complex. 71.58 g of molybdic acid (Aldrich, $MoO_3 \geqq 85.0\%$) was added to 260.16 g of benzene carboxylic acid (98%) in a 500 ml flask. The flask was connected to a receiver and condenser, to allow water vapor to escape. The flask was purged with $N_2$ at 220 ml per minute for about 10 minutes and then switched to $H_2$ at 220 ml per minute. The flask was then placed in a silicone oil and the temperature of the mixture was raised to 210-220° C. and held for 15 hours. After cooling to room temperature the Mo content was calculated to be 14.0 wt % Mo.

Example 3

Preparation of Bimetallic Catalyst

Example 3 describes the preparation of a bimetallic catalyst. 275.41 g of the Mo catalyst prepared in Example 2 was placed into a metal vessel and the vessel was purged with nitrogen. Then, 200.15 g of the oil soluble nickel catalyst of Example 1 was added to the Mo catalyst with continuous stirring and with a nitrogen purpose. The mixture included 10 wt % metals.

Example 4

Light Cycle Oil to Monoaromatics

Example 4 describes the use of the catalyst of Example 3 to upgrade light cycle oil (LCO) by increasing the wt % of monoaromatic compounds. The LCO feedstock was 16.3% monoaromatics and 81.3 diesel, with negligible BTX or gasoline. A diluted catalyst was prepared by diluting 476 g of the catalyst of Example 1 in 1928 gms of LCO to make 2404 g slurry with 2 wt % metal concentration. The sample was then mixed with LCO to produce a fresh feed with 400 wppm metal.

The reaction was run under reaction temperature 779° F., reaction pressure 1400 psig, the feed rate of fresh feed was 350 g/hr, and with 50% O-6 recycle. Samples were taken and held separately every 24 hours. The reaction results were following: BTX yield 20.4%, Gasoline/Diesel yield 70.8%, 3.7% of $C_1$-$C_7$ (LPG) and 5.7% of VGO (The foregoing BTX yield includes straight chain and branched alkyl groups attached to aromatic rings).

Example 5

Pyrolysis Fuel Oil to Monoaromatics

Example 5 describes the use of the catalyst precursor of Example 3 to upgrade pyrolysis fuel oil (PFO) by increasing the wt % of monoaromatics compounds. The PFO feedstock included 11.4% monoaromatics, 53.0% diesel, and negligible BTX or gasoline. A diluted catalyst was prepared by diluting 476 g of the catalyst of Example 3 in 1928 g of VGO oil to make 2404 g slurry with 2 wt % metal concentration at 120° F. The sample was then mixed with PFO to produce a fresh feed with 400 wppm metal at 120° F.

The reaction was run under reaction temperature 779° F., reaction pressure 1400 psig, the feed rate of fresh feed was 350 gms/hr, and with 50% O-6 recycle. Samples were taken and held separately every 24 hours. The reaction results were the following: BTX yield 17.0%, Gasoline/Diesel yield 72.3%, 3.6% of $C_1$-$C_7$ (LPG), 5.0% of VGO, and 3.2% of resid (The foregoing BTX yield includes straight chain and branched alkyl groups attached to aromatic rings).

As demonstrated in the examples, the catalyst and process of the present invention can increase the monoaromatic content of hydrocarbon feedstocks that include polynuclear aromatics. Surprisingly the increase in monoaromatics can be achieved with an increase in gasoline/diesel yields and while reducing unwanted compounds. Because the upgrading process of the invention yields high value mono-aromatics, while maintaining and/or increasing the content of other valuable products, the present invention provides a feasible route for upgrading hard-to-upgrade hydrocarbons that include significant quantities of polynuclear aromatics.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. An oil-soluble catalyst for hydrocracking a hydrocarbon feedstock containing polynuclear-aromatics, comprising:
   an oil-soluble catalyst complex comprised of:
   a first catalytic metal atom selected from the group consisting of group VIB metals, group VIIIB metals, and combinations thereof;
   a second catalytic metal atom selected from the group consisting of group VIB metals, group VIIIB metals, and combinations thereof; and
   an organic ligand bonded with the first and second catalytic metal atoms, wherein the organic ligand is comprised of:
   an aromatic group;
   a first ligand spacing group bonded to the aromatic group, the ligand spacing group having an atom bonded to the first metal atom and another atom bonded to the aromatic group and providing separation of 2-6 atoms between the first metal atom and the aromatic group; and
   a second ligand spacing group bonded to the aromatic group, the ligand spacing group having an atom bonded to the second metal atom and another atom bonded to the aromatic group and providing separation of 2-6 atoms between the second metal atom and the aromatic group.

2. A catalyst as in claim 1, wherein the first ligand spacing group comprises an acid residue group.

3. A catalyst as in claim 2, wherein the acid residue comprises B, N, P, S, or C.

4. A catalyst as in claim 1, wherein the first ligand spacing group comprises at least one side group.

5. A catalyst as in claim 4, wherein the side group comprises an oxygen or an alkoxy group.

6. A catalyst as in claim 1, wherein the aromatic group comprises a five member or six member ring.

7. A catalyst as in claim 1, wherein the aromatic group is alkylated.

8. A catalyst as in claim 1, wherein at least one of the first or second catalytic metal atoms is selected from the group consisting of tungsten (W), molybdenum (Mo), chromium (Cr), nickel (Ni), cobalt (Co), iron (Fe), vanadium (V), titanium (Ti), manganese (Mn), and combinations thereof.

9. A catalyst as in claim 1, wherein the catalyst complex comprises at least two different types of catalytic metal atoms.

10. A catalyst as in claim 9, wherein the metal atoms comprise Mo and at least one other Group VIB or Group VIIIB metal.

11. A catalyst as in claim 1, wherein the catalyst includes a plurality of oil-soluble catalyst complexes and wherein at least some of the oil-soluble catalyst complexes are linked together so as to form an extended network of intercomplexed ligands and metal atoms.

12. A catalyst as in claim 1, wherein the aromatic group includes a benzene ring.

13. A method for increasing the monoaromatic content of a hydrocarbon material containing polynuclear aromatic compounds comprising hydrocracking the hydrocarbon material in the presence of the catalyst of claim 1 or a derivative thereof.

14. A method as in claim 13, wherein the concentration of catalyst in the hydrocarbon material during hydrocracking is in a range from about 1 ppm to about 1,000 ppm.

15. An oil soluble catalyst comprising a complex according to the following structure:

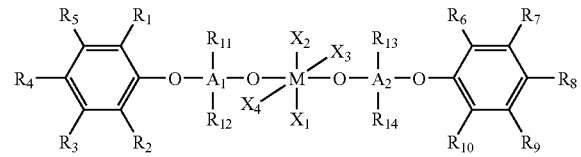

wherein,
M is a group VIB metal, a group VIIIB metal, or a base transition metal;
$R_1$-$R_{10}$ are independently a hydrogen, an alkyl group, or a bond to a ligand spacing group that is bonded to another metal atom;
$A_1$ and $A_2$ comprise a single atom or a chain of atoms, at least one of the atoms being selected from the group consisting of B, N, P, S, group IIIA elements, group IVA elements, group VA elements, and group VIA elements;
$R_{11}$-$R_{14}$ are independently a single bonded oxygen, a double bonded oxygen, or an alkoxide; and
$X_1$-$X_4$ are optional ligands bonded to the catalytic metal.

16. An oil soluble catalyst as in claim 15, wherein M is W, Mo, Cr, Ni, Co, Fe, V, Ti, or Mn.

17. A catalyst as in claim 15, wherein at least one of $R_1$-$R_6$ and one $R_7$-$R_{10}$ are an alkyl group having between 1 and 12 carbons.

18. A catalyst as in claim 15, wherein the catalyst comprises a plurality of oil-soluble catalyst complexes linked together to form an extended network of intercomplexed ligands and metal atoms.

19. A method for increasing the mono-aromatic content of a hydrocarbon material containing polynuclear aromatics, comprising hydrocracking the hydrocarbon material in the presence of the catalyst of claim 15.

20. A method as in claim 19, wherein the concentration of catalyst in the hydrocarbon material during hydrocracking is in a range from about 1 ppm to about 1,000 ppm.

21. A catalyst for hydrocracking a hydrocarbon feedstock containing polynuclear-aromatics, comprising:
   a plurality of oil soluble catalyst complexes comprised of, a plurality of catalytic metal atoms comprising Mo and at least one other Group VIB or Group VIIIB metal;

a plurality of organic ligands complexed with each of the metal atoms, each organic ligand comprising, an aromatic group; and at least one ligand spacer group bonded to the aromatic group, wherein the ligand spacer group is comprised of an acid residue that is bonded to the aromatic group and to the metal atom and wherein the spacer group provides separation of 2-4 atoms between the metal atom and the aromatic group, wherein at least some of the oil-soluble catalyst complexes are linked together to form an extended network of inter-complexed ligands and metal atoms.

22. A catalyst as in claim 21, wherein the acid residue comprises a side chain group.

23. A catalyst as in claim 21, wherein a molar ratio of the Mo to the at least one other Group VIB or Group VIIIB metal is in a range from about 50:1 to about 1:20.

24. A catalyst as in claim 21, wherein the aromatic group includes a benzene ring.

25. A method for increasing the monoaromatic content of a hydrocarbon material containing polynuclear aromatics, comprising hydrocracking the hydrocarbon material in the presence of the catalyst of claim 21.

* * * * *

UNITED STATES PATENT AND TRADEMARK OFFICE
CERTIFICATE OF CORRECTION

PATENT NO. : 7,951,745 B2  
APPLICATION NO. : 11/968861  
DATED : May 31, 2011  
INVENTOR(S) : Zhou et al.

Page 1 of 1

It is certified that error appears in the above-identified patent and that said Letters Patent is hereby corrected as shown below:

<u>Face, Left Hand Column, Item #73, Assignee</u>

Change "Wilmington Trust FSB, Minneapolis, MN (US)" to --Headwaters Technology Innovation, LLC, Lawrenceville, NJ (US)--

Signed and Sealed this
Twenty-ninth Day of January, 2013

David J. Kappos
*Director of the United States Patent and Trademark Office*